United States Patent
Ernst, Jr. et al.

(10) Patent No.: US 10,485,690 B2
(45) Date of Patent: Nov. 26, 2019

(54) PERSONAL EQUIPMENT SUSPENSION SYSTEM WITH ACTIVE LUMBAR SUPPORT

(75) Inventors: Craig E. Ernst, Jr., Marlboro, NY (US); Jeffrey D. Anderson, Hampshire, IL (US); Christopher A. J. Iannello, Rolling Meadows, IL (US); Martin J. Nilsen, Hampshire, IL (US); David A. Shereyk, Des Plaines, IL (US); Timothy P. Coffield, Grand Rapids, MI (US)

(73) Assignee: Illinois Tool Works Inc., Glenview, IL (US)

( * ) Notice: Subject to any disclaimer, the term of this patent is extended or adjusted under 35 U.S.C. 154(b) by 178 days.

(21) Appl. No.: 13/978,172

(22) PCT Filed: Jan. 5, 2012

(86) PCT No.: PCT/US2012/020338
§ 371 (c)(1),
(2), (4) Date: Jul. 3, 2013

(87) PCT Pub. No.: WO2012/094499
PCT Pub. Date: Jul. 12, 2012

(65) Prior Publication Data
US 2013/0283492 A1    Oct. 31, 2013

Related U.S. Application Data

(60) Provisional application No. 61/488,893, filed on May 23, 2011, provisional application No. 61/467,534, (Continued)

(51) Int. Cl.
*A61F 5/02* (2006.01)

(52) U.S. Cl.
CPC .................................. *A61F 5/028* (2013.01)

(58) Field of Classification Search
CPC .................................. A45F 3/08; A45F 3/047
(Continued)

(56) References Cited

U.S. PATENT DOCUMENTS 3,265,260 A * 8/1966 Romney ........................ 224/161
3,355,075 A * 11/1967 Dean ............................ 224/262
(Continued)

FOREIGN PATENT DOCUMENTS

EP    1607028 A2    12/2005
WO    9806297 A1    2/1998

OTHER PUBLICATIONS

International Search Report and Written Opinion corresponding to PCT/US2012/020338, dated Feb. 20, 2012.

*Primary Examiner* — Derek J Battisti
(74) *Attorney, Agent, or Firm* — Quarles & Brady LLP

(57) ABSTRACT

A personal equipment suspension system with active support to the lumbar region includes a belt to surround the user's waist and a frame supported on the belt with a resilient membrane of synthetic elastomeric crystalline material in tension on the frame to be interposed between the belt and the user. The frame includes spaced ends and the membrane is a lattice in tension between the spaced ends. In one embodiment, the system is a support belt. In another, it is load bearing such as a backpack configuration. In another, it includes stanchions to support a body armor vest.

9 Claims, 9 Drawing Sheets

Related U.S. Application Data filed on Mar. 25, 2011, provisional application No. 61/430,246, filed on Jan. 6, 2011.

(58) Field of Classification Search
USPC .................... 224/633, 637, 645, 627, 631
See application file for complete search history.

(56) References Cited

U.S. PATENT DOCUMENTS

| | | | | |
|---|---|---|---|---|
| 3,797,718 | A * | 3/1974 | Plant | 224/262 |
| 4,040,548 | A * | 8/1977 | Guglielmo | 224/262 |
| 4,214,685 | A * | 7/1980 | Pletz | 224/634 |
| 4,361,259 | A * | 11/1982 | Chanter | 224/635 |
| 4,911,346 | A * | 3/1990 | Shallman | 224/631 |
| 5,611,457 | A | 3/1997 | Ash, Jr. | |
| 5,890,640 | A * | 4/1999 | Thompson | 224/630 |
| 5,954,253 | A * | 9/1999 | Swetish | A45F 3/08 |
| | | | | 224/628 |
| 6,199,732 | B1 * | 3/2001 | Swetish | A45F 3/04 |
| | | | | 224/262 |
| 6,662,981 | B2 * | 12/2003 | McUmber | A45F 3/10 |
| | | | | 224/155 |
| 7,287,677 | B2 * | 10/2007 | Reid | 224/637 |
| 2006/0151559 | A1 * | 7/2006 | Gravseth | 224/637 |
| 2006/0266781 | A1 * | 11/2006 | Howell | 224/628 |
| 2006/0267258 | A1 | 11/2006 | Coffield et al. | |
| 2008/0179367 | A1 * | 7/2008 | Storey | 224/637 |
| 2010/0076359 | A1 * | 3/2010 | Glenn | 602/19 |
| 2010/0243693 | A1 * | 9/2010 | Terry et al. | 224/633 |
| 2011/0108595 | A1 * | 5/2011 | Hoag | 224/633 |
| 2012/0000948 | A1 * | 1/2012 | Maggi | 224/262 |

\* cited by examiner

PERSONAL EQUIPMENT SUSPENSION SYSTEM WITH ACTIVE LUMBAR SUPPORT

CROSS REFERENCE TO RELATED APPLICATION

This application is a National Phase of International Application Number PCT/US2012/020338, filed Jan. 5, 2012, and claims the benefit of U.S. Provisional Application 61/430,246 filed Jan. 6, 2011, U.S. Provisional Application 61/467,534 filed Mar. 25, 2011, and the benefit of U.S. Provisional Application 61/488,893 filed May 23, 2011.

BACKGROUND

This disclosure relates to personal equipment suspension systems for manual load bearing. More particularly, it relates to personal equipment suspension systems with active support to the lumbar region of the user.

Personal equipment suspension systems for personal load bearing take many forms. Generally, they surround the user's body and transfer load to the user's torso at the hip area. They find application in a wide variety of disciplines including construction, medical-EMS, military, law enforcement, sports, and outdoor activities such as hunting, fishing, camping, hiking, climbing, gardening and the like.

Lumbar suspension system embodiments can be utilized for specific "lumbar" support, as is typically provided for warehouse, dock or construction workers and load lifting occupations or athletic activities. Current lumbar belt supports are constructed from elastic bands and may include a latching belt. These current products support the body by applying the belt tightly around the user and greatly increasing the hoop stress or hydrostatic pressure in the abdomen as to offset the necessary support for the lumbar region of the body.

Personal support belts for use in load lifting environments or tool belts used in home improvement and construction are used to carry tools or other equipment for construction, landscape, telecommunications, or home improvement activities. Typically such belts consist of a belt of leather or woven fabric made from Nylon, or other polymer, and include attachment points for personal equipment or gear, or pouches to hold items such as a hammer, nails, or other job specific items.

The belt surrounds the waist of a user. In the most advanced form, such belts may also include a shoulder harness that helps support the load of the fully weighted belt and gear. The belt and shoulder harness do not offer the user any improved comfort or ergonomically designed lumbar support. Biomechanical research has shown the "S-Curve" or lumbar curvature known as lordosis is a natural position of the body when standing. This position acts to support the body and efficiently transfer loads through the body into the lower extremities. Under normal use of current belts, this natural position disappears as the loading causes the hips to rotate and produce additional strain on the lumbar muscular region. This strain increases user fatigue and discomfort.

Personal equipment suspension systems are employed in trekking, hiking, and other outdoor adventure activities for carrying of loads such as clothing and supply backpacks, or outdoor equipment including tents, cooking equipment or even watercraft.

Various arrangements exist for load distribution, reduction of impact or pressure points and protection of the user from discomfort or injury. Significant in this regard is the protection of the spine, and the lumbar area. It is considered desirable to provide support for, or distribution from, a carried load, to the user's torso, at or near the lumbar area, that is, immediately above the user's waist at the back of the spine. Known arrangements for providing such capability are inflatable or liquid filled, with the attendant frailties of bladder type devices.

In carrying unusually bulky or heavy loads such as camping or climbing equipment, tents, cooking equipment, and even canoes or similar watercraft, distribution and balance of the carried load are important attributes of a personal transport system. Often, such equipment delivers the carried load through spaced vertical spines or structural tubes connected to an associated support belt. Traversing rough terrain with such equipment sometimes results in unbalance or other difficulties. Moreover, undue fatigue and/or strain is often associated with the task.

SUMMARY OF DISCLOSURE

The active lumbar support system embodiments of the present disclosure significantly improve comfort, support, and ergonomics when integrated into a personal equipment suspension system. The suspension system resiliently supports the lumbar region while allowing the body to maintain the desired lordosis.

The arrangements of this disclosure allow users to attach the improved suspension system to the waist/hip/torso area of the body, and secure the system belt within a tolerable level of "tightness." The improved suspension system provides immediate support and comfort in the lumbar area of the body. A suspension membrane gives active load dampening while maintaining lumbar region support. The membrane of molded elastomeric material prevents material creep over a wide range of loading conditions and for an indefinite amount of time. The molded membrane suspension can be designed to include improved airflow similar to a open mesh form which reduces thermal build up and discomfort for the user as well.

The disclosed arrangement improves the support and comfort over current lumbar supports, by providing an ergonomic specific shape, a non-creep elastomeric membrane, and improved air flow and comfort. As the user applies the necessary belt tightening force, the elastomeric suspension membrane acts to counter the applied tightening force which provides immediate support force to the desired area of the lumbar. The suspension system membrane provides a "preloaded" force which allows for maximum support with minimal belt tightening.

The personal equipment suspension system with active lumbar support of the present disclosure addresses the foregoing aspects of personal load carrying and provides unique, desirable and viable solutions. The present disclosure is directed to a personal equipment suspension system that is lightweight, ergonomic and physically comfortable. It represents a suitable personal equipment suspension solution useful in a variety of markets and disciplines including home improvement, juvenile products, construction, hunting, fishing, law enforcement, medical, exercise, sporting, and military applications; and other "waist/hip" equipment harness applications. It provides active lumbar support to the user.

DETAILED DESCRIPTION

Figure 1:
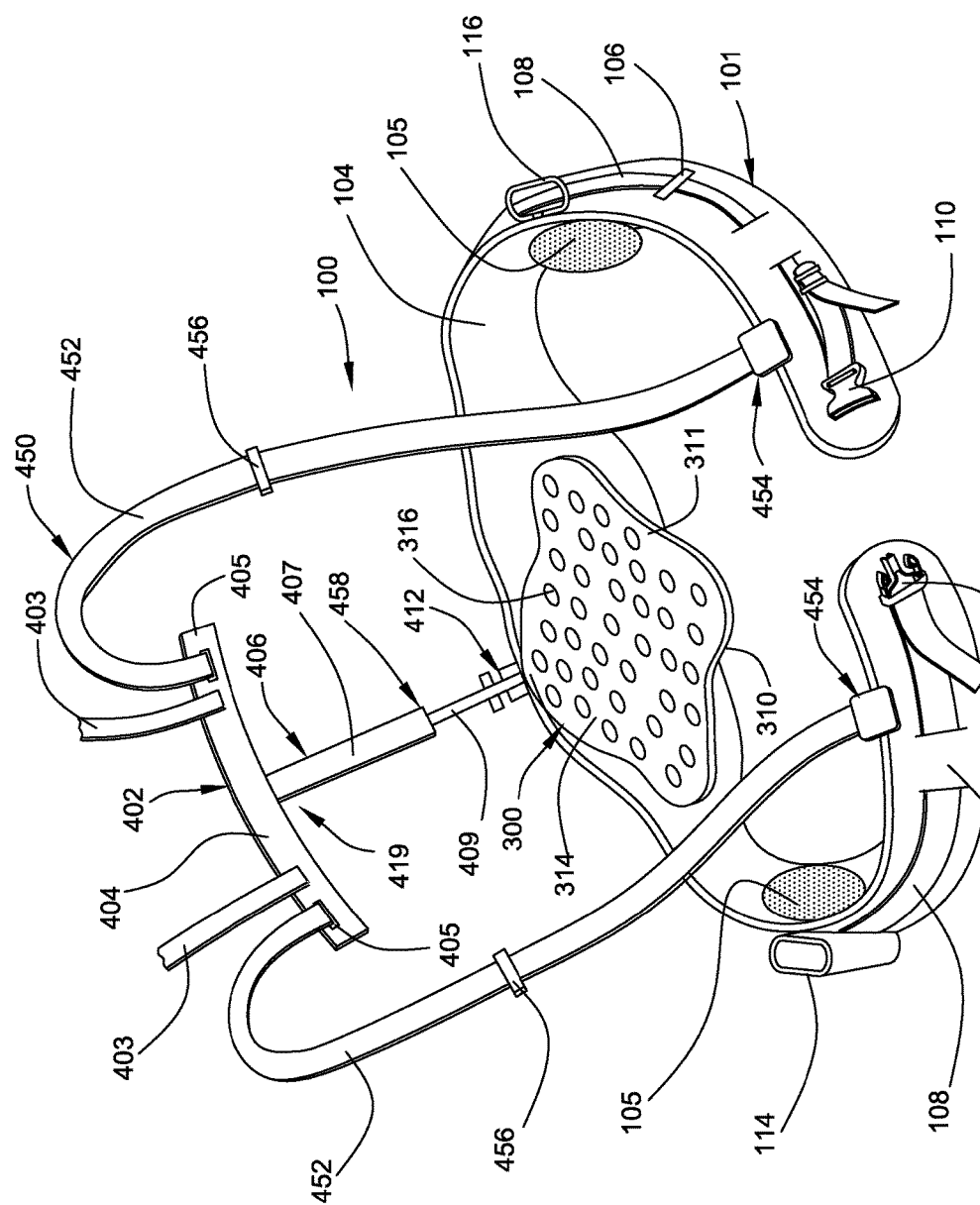
FIG. 1 is a perspective view of a personal equipment suspension system illustrative of the features of the present disclosure.

FIG. 1 shows a personal equipment suspension system, generally designated 100, illustrative of the features of the present disclosure. System 100 is a specific illustrative embodiment of a personal equipment suspension system providing the features and advantages of active lumbar support contemplated by the disclosure. It, and the illustrations of various other or modified embodiments contained herein are only illustrative and not limiting. Numerous variations and configurations suitable to specific uses or applications are envisioned within the scope of this disclosure.

The illustrated personal equipment suspension system 100 includes a waist encircling belt 101 having a relatively wide main web 104, for example, of heaving duty nylon fabric internally padded with ergonomic foam, gel, or similar soft material for comfort against the user's body at key load bearing areas such as the hips or lower back. As illustrated, the main web 104 may optionally include additional pads, such as gel pads 105 removably attached at the hip contact areas on either side of the belt 101.

The exterior of web 104 is provided with a series of spaced, vertically disposed loops 106. The main web 104 is integrated with an attachment strap 108 that passes through the loops 106 to form an integral belt assembly. Made of nylon webbing, it includes a center buckle element 110 and latch element 112 which are releasably connectable about the wearer. The strap 108 and buckle and latch elements are configured to permit adjustment of the strap 108 surrounding the user to cinch up the belt 101 about the user to a tightness suitable for the particular usage involved and also maintain the buckle element 110 and latch element 112 centrally positioned in front of the user for easy manipulation. It is contemplated that a suitable buckle and latch arrangement is available from ITW Nexus, Des Plaines, Ill.

Belt 101 may include any number of equipment receiving attachments. Illustrated here are a pocket 114 to receive, for example, a tool or a communication device, and a ring 116 to receive any form of accessory attachment.

Centrally positioned internally of the waist encircling belt 101 of personal equipment suspension system 100 is active lumbar support mechanism 300. This mechanism is intended to actively urge against, and support the wearer's lumbar region. It is also arranged to deliver a portion of any load received by the system 100 over the lumbar region of the user's back, at the lower spine. It is determined that such placement of the load burden is ergonomically beneficial and reduces the negative impact of load carrying. The result is less fatigue and reduced propensity for injury to the wearer.

Notably, it is contemplated that the system 100, as configured with the active lumbar support mechanism 300, would find beneficial application in, for example, athletic endeavors such as free weight lifting or other strenuous load lifting activity where lumbar support is deemed beneficial or desirable.

Active lumbar support mechanism 300 includes lumbar distribution plate 310. Lumbar distribution plate 310, seen in FIGS. 1 and 2, may take any shape to conform with assured contact with the user's back over a wide area of the lumbar region. It is here illustrated as generally oblong, with a complex curved perimeter having a generally rigid perimeter rim or frame 311. It defines a body contact surface for contact with the user when the personal equipment suspension system is worn. It is contemplated that the plate 310 be a molded polymeric member with a formed lattice of resilient webs 314 defining interposed apertures 316. The lattice is in tension and on deformation applies a restoring force against the user's lumbar region. The lattice configuration also provides for weight reduction and ventilation.

It is contemplated that load distribution plate 310 may advantageously be formed using high-tech synthetic crystalline elastomeric material developed and marketed by ITW Dahti, Rockford, Mich. A suitable material is disclosed in U.S. Pat. No. 7,441,758 issued Oct. 28, 2008, entitled "Load Bearing Surface" assigned to Illinois Tool Works, Inc. The entire specification and drawings of this patent are incorporated by reference herein as if fully set forth.

Plate 310 is an elastomeric structure which forms a highly compliant membrane that offers superior comfort. The membrane is processed to provide orientation of the crystalline structure to create a compliant, robust, lively and resilient spring that will not creep or sag under all operating conditions by ITW-Nexus, Des Plaines, Ill. and ITW-Shanghai, China. It is cost effective, light weight and adaptable to thin profiles.

Figure 2:
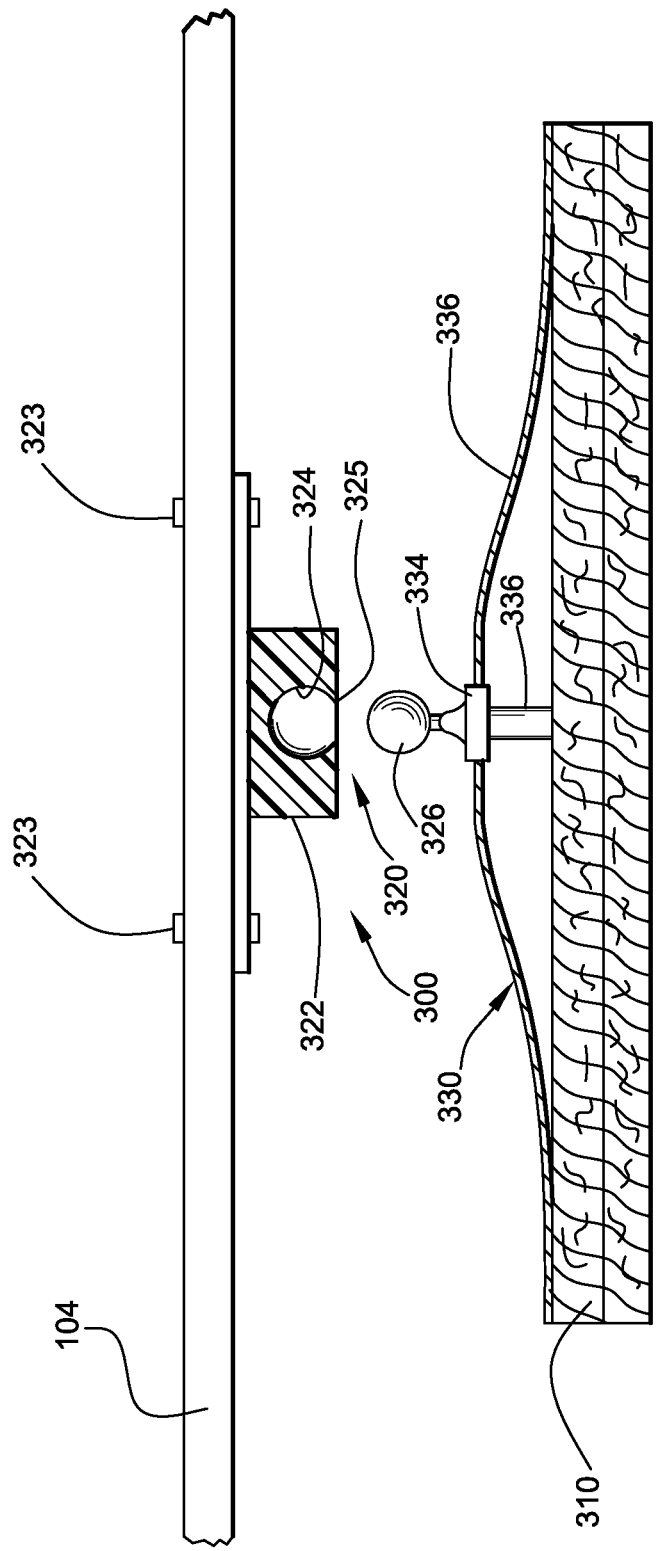
FIG. 2 is a fragmentary top view, partially in section, of the active lumbar support mechanism of the personal equipment suspension system of FIG. 1.

Lumbar distribution plate 310 of active lumbar support mechanism 300 illustrated in FIGS. 1 and 2 is supported on the interior of wide main web 104 of belt 101 by swivel joint mechanism 320 through biasing arm assembly 330. Swivel joint mechanism 320 seen in FIG. 3, includes a mounting bracket 322 secured to a main web 104 of belt 101 with fasteners 323. Bracket 322 defines a spherical socket receptacle 324, the open mouth 325 of which is slightly smaller than the maximum spherical diameter of the receptacle. Swivel joint mechanism 320 includes a complementary ball 326 associated with biasing arm assembly 330. It is engaged within receptacle 324. These components may be made of rigid plastic such as Acetal and "snap" together to form the swivel joint mechanism.

Biasing arm assembly 330 includes base 334 and a plurality of resilient bows 336 that extend between base 334 and lumbar distribution plate 310. Ball 326 is mounted on biasing arm assembly 330 at base 334.

Bows 336 are resilient flexible members and are stressed by compressive deformation on securement of the personal equipment suspension system 100 about the user's waist. The amount of compression of bows 336 is controlled by manual adjustment of the length of the attachment strap 108 relative to the buckle 110 and latch 112. This compression of the bows 336 and resultant restoring force created imparts a force to the lumbar distribution plate 310 that urges the plate 310 against the wearer's back at the lumbar region. The articulated connection of the lumbar distribution plate 310 and belt 101 through swivel joint mechanism 320 insures uniform application of these forces against the user to maximize comfort and lumbar area protection.

As illustrated in FIG. 1, the personal equipment suspension system 100 is equipped with a shoulder harness 450 which includes spaced shoulder straps 452 that releasably connect to main web 104 in spaced relation to buckle 110 and latch 112.

Straps 452 are spaced for comfortable contact support on the user's shoulders. They terminate in buckles and latches at connections 454 for easy connection and disconnection to main web 104. Clips 456 permit length adjustment to assure a snug fit against the wearer's shoulders. Such buckles, latches, and adjustment clips are commercially available from ITW Nexus, Des Plaines, Ill.

Figure 4:
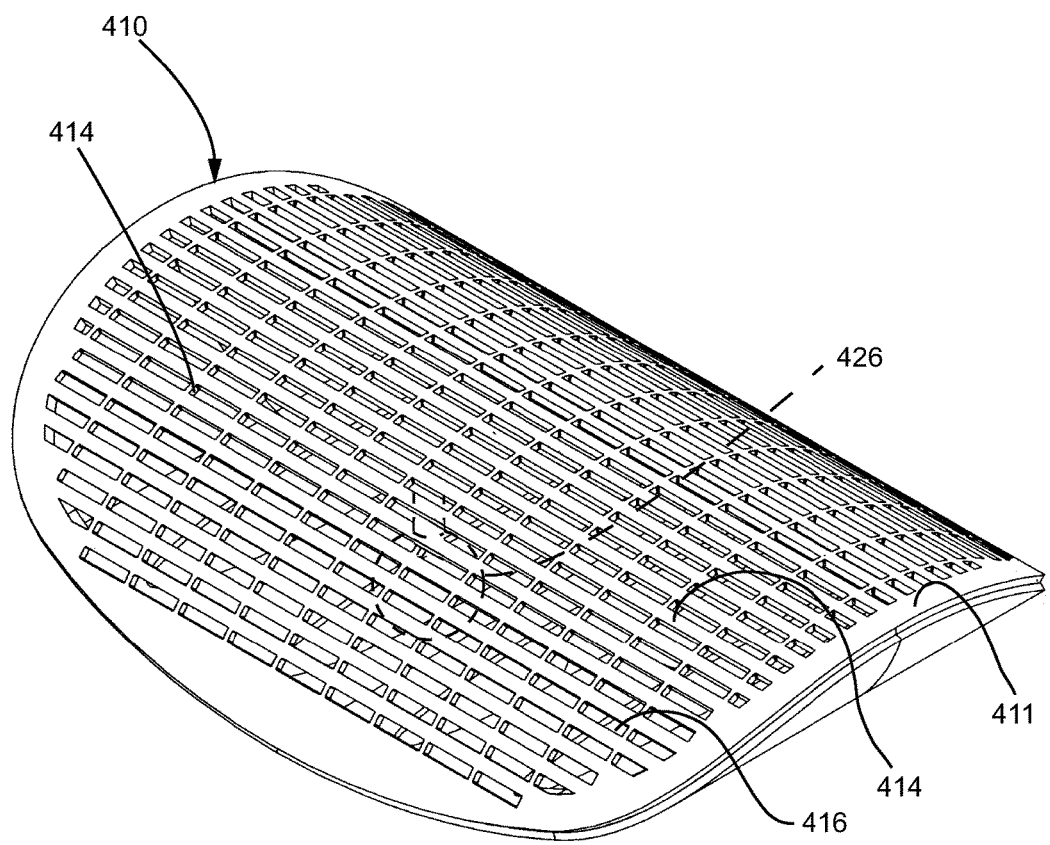
FIG. 4 is a perspective view of a slightly modified form of a portion of the active lumbar support mechanism of the personal equipment suspension system of FIG. 1.

Another possible configuration for load distribution plate 310 of a molded component of material with a rigid perimeter rim or frame and resilient lattice web is seen in FIG. 4. There a generally oval shaped load distribution plate 410 is illustrated. Again it is contemplated that the plate 410 include a perimeter rim or frame 411. The illustrated plate is formed of the Dahti material, which is a semi-rigid, synthetic elastomeric crystalline material. It includes resilient lattice webs 414 defining formed apertures 416.

Distribution plate 410 includes a connection ball 426. It may be supported upon belt 101 by a swivel joint mechanism such as swivel joint mechanism 320 or any other suitable means. It is, of course, positioned for resilient contact with the user's back at the lumbar region and is shaped accordingly.

Figure 3:
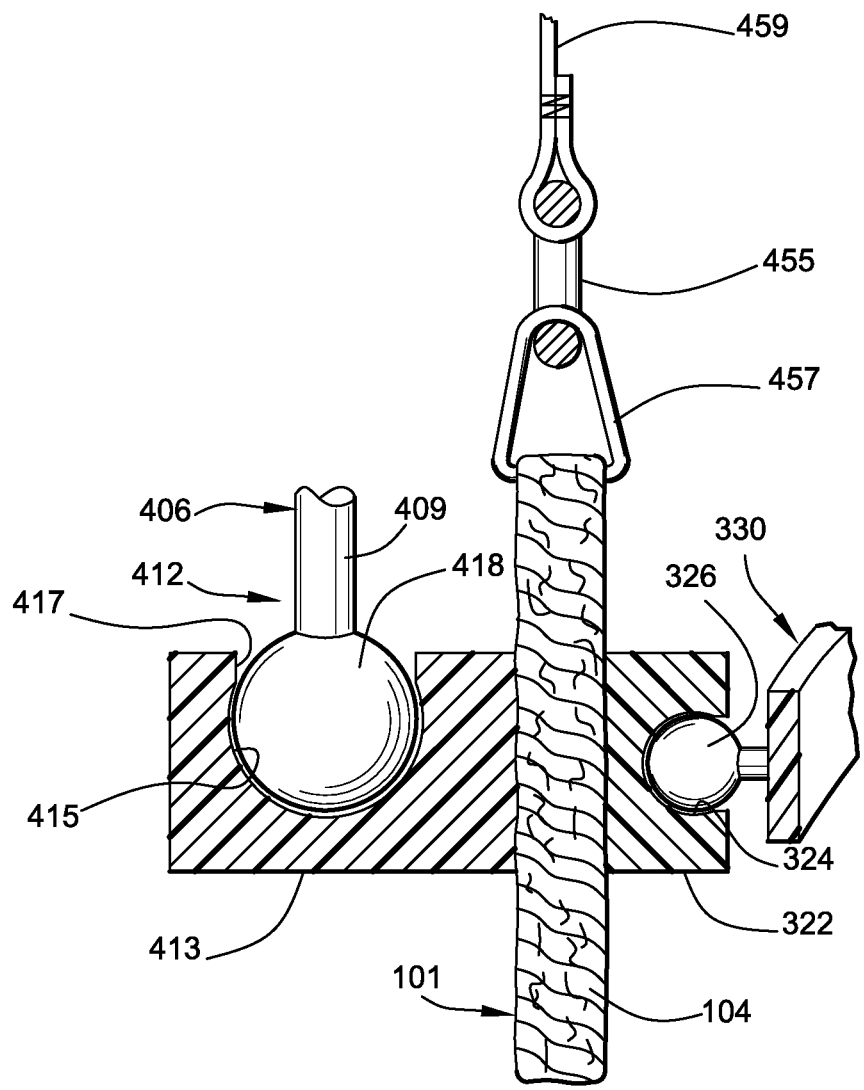
FIG. 3 is a fragmentary side view, partially in section, of the active lumbar support mechanism of the personal equipment suspension system of FIG. 1.

As illustrated in FIGS. 1 and 3, personal equipment suspension system 100 is connected to a carried load through articulated flexible load suspension mechanism 419. It has a load support bracket 402 secured to the rear midpoint of the personal equipment suspension system 100 at the spine area by a swivel joint mechanism 412. Load support bracket 402 includes transverse bar 404 with spaced eyelets 405 and a central vertical beam 406 extending between transverse bar 404 and swivel joint mechanism 412. Eyelets 405 receive and connect to straps 452 of shoulder harness 450. Load to be carried is applied to load support bracket 402 through any convenient connection such as, for example, attachment straps 403.

Transverse bar 404 is arranged to be secured to any load to be carried. It would include any necessary attachment mechanism for receiving a load, for example, in the form of a backpack, equipment pack such as a leaf blower or lawn trimmer, or support bracket extending upward to an applied load such as a carried watercraft.

Vertical beam 406 includes segments 407 and 409 slidably engaged at slide joint 458 to permit adjustment of its overall length. Slide joint 458 permits vertical positioning of transverse beam 404 by the user to accommodate personal preference or variation in user height.

Best seen in FIG. 3, swivel joint mechanism 412 includes a bracket 413 mounted to the exterior surface of main web 104 of personal equipment suspension system 100 centrally at the midpoint, outward of mounting bracket 322 associated with active lumbar support mechanism 300. Bracket 413 defines a spherical, ball receiving receptacle or socket 415 facing upwardly. It includes an open mouth 417 slightly smaller than the maximum spherical diameter of the ball receiving receptacle.

Lower segment 409 of vertical beam 406 terminates at its lower end in a ball 418 sized to be received in spherical receptacle 415 to form an articulated connection. The ball 418 and socket 415 are made of plastic material such as Acetal and "snap" together.

Load received by horizontal transverse bar 404 is delivered to the personal equipment suspension system 100 through the swivel joint mechanism 412. The load is thereby transferred to the personal equipment suspension system 100 by the articulated flexible load suspension mechanism 419 which ensures that it remains balanced and accommodates lateral, sideways, or forward and backward movements of the user.

The load applied to transverse bar 404 is shared with shoulder harness 450. The adjustment clips 456 can be used to adjust the length of the shoulder straps 450 and consequently the amount of load carried respectively by the shoulder harness and the articulated flexible load suspension mechanism 419.

Personal equipment suspension system 100 is illustrated in FIG. 1 as including load suspension mechanism 419 having articulated flexible connection 412 for balanced load carrying. As already explained, waist encircling belt 101 with active lumbar support mechanism 300 is useful alone, without load suspension mechanism 419, in instances where active lumbar support alone provides a desirable benefit.

It is also contemplated that belt 101 could be used for load carrying with only shoulder harness elements similar to those associated with the articulated flexible load suspension mechanism 419. In such instance, for example, as illustrated in FIG. 3, belt 101 may be provided with a "D" ring 455 secured to main web 104 by a clip 457. A connection strap 459 extends vertically upward from "D" ring 455 and attaches to a transverse bar, such as transverse bar 404 of FIG. 1, equipped with shoulder straps, such as shoulder straps 452. In this arrangement, vertical beam 406 would not be employed.

Figure 5:
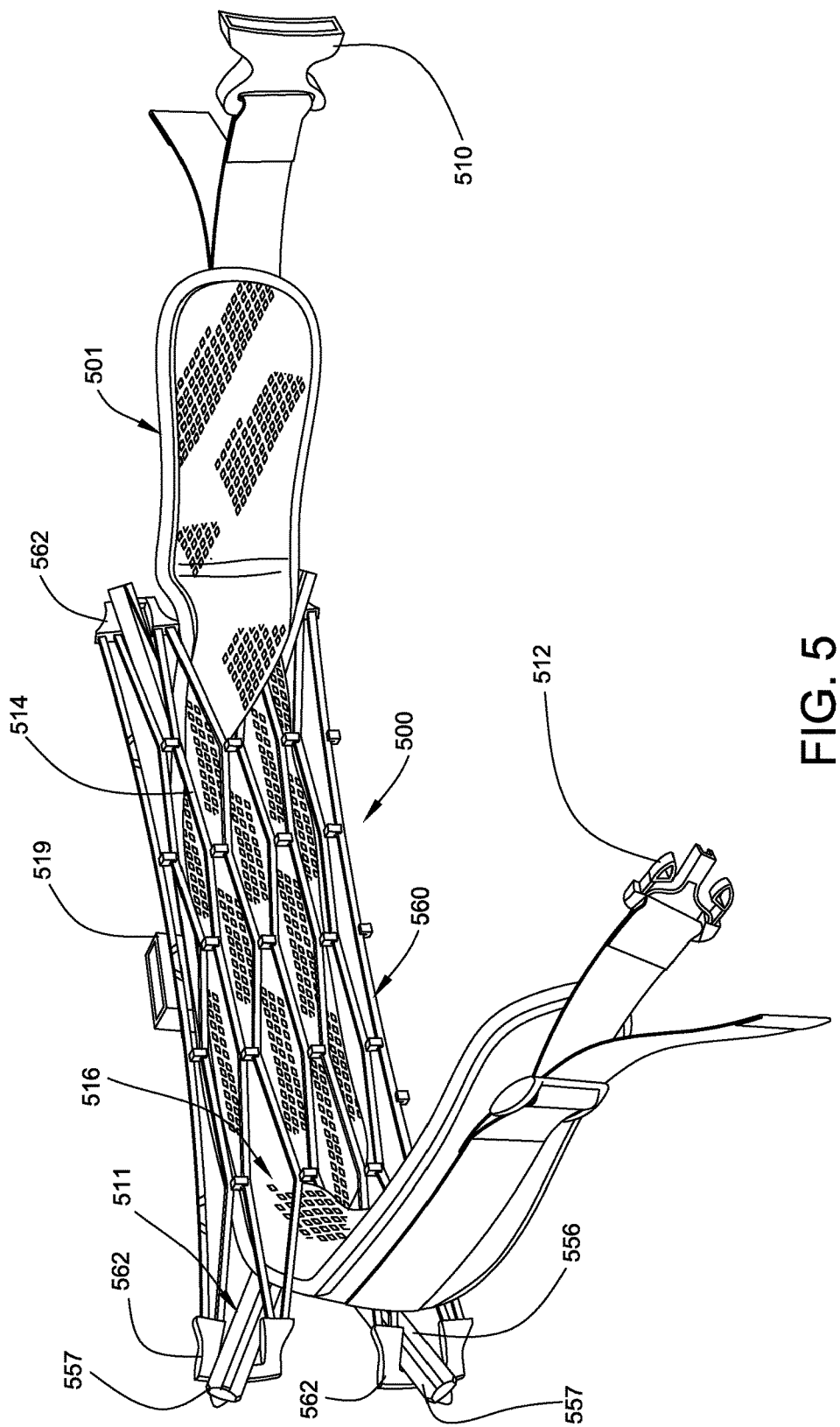
FIG. 5 is a front perspective view of a personal equipment suspension system with active lumbar support illustrative of the principles of the present disclosure.
Figure 6:
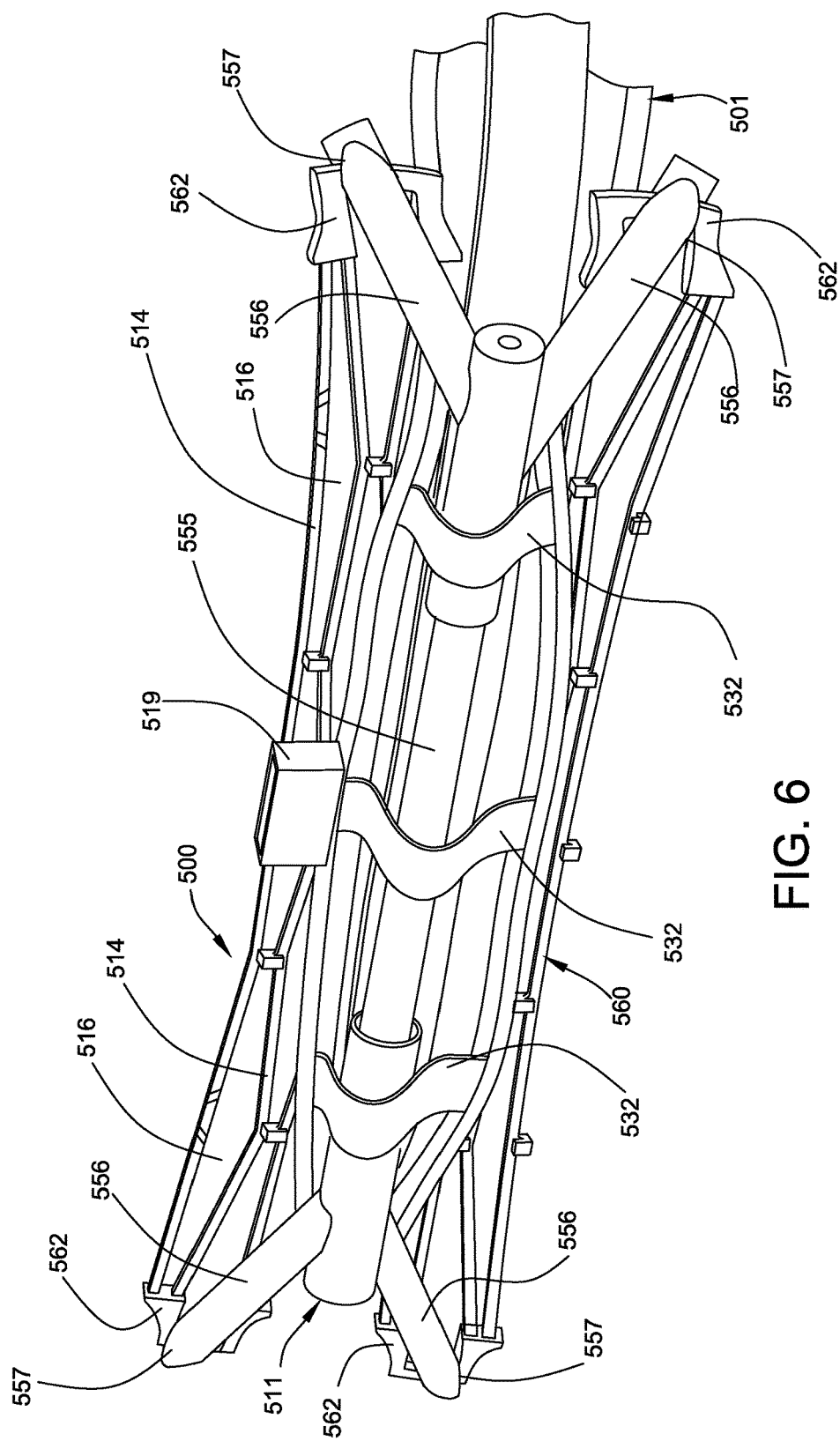
FIG. 6 is a rear perspective view of the personal equipment suspension system with active lumbar support illustrated in FIG. 5.

Another example of a personal equipment suspension system that provides the advantages of active lumbar support as contemplated herein is illustrated in FIGS. 5 and 6. A personal equipment suspension system with active lumbar support is shown. As illustrated, the system includes a user belt or harness, generally 501, a load suspension mechanism in the form of connection pocket 519, and an active lumbar support mechanism 500. Pocket 519 is adapted to receive a rigid vertical load receiving member which receives the weight of the load within a pouch or similar load receiving container.

Belt 501 includes connection buckle components 510 and 512 at opposite ends to surround the user's waist for load distribution to the hip area. The load receiving member 519 is connected to belt 501 midway between its ends. When, for example, an assembly embodying the belt 501 is worn by a user, the load suspension mechanism 519 is generally aligned with the user's spine.

As shown, active lumbar support mechanism 500 of the present disclosure is interposed between the load suspension mechanism 519 and the user's back. It provides a comfortable and ergonomically advantageous partial distribution of the carried load directly to the user's back. It includes a rigid frame 511 connected to the exterior surface of the belt 501 by straps 532 best seen in FIG. 6. Frame 511 may be generally arc shaped to complement the shape of a user's body. It includes horizontal bar 555 with yokes 556 at opposite ends defining attachment terminals 557.

A flexible membrane 560 is stretched between the attachment terminals 557 of frame member 511 and placed in tension between the yokes 556. It includes webs 514 defining voids or apertures 516. In this embodiment, the membrane includes elastomeric connector pads 562 at the ends of webs 514 connected to attachment terminals 557 of frame member 511. It is arranged such that in use, the membrane 560 contacts the user's lumbar region.

On connection of the buckle components 510 and 512, the membrane 560 is stretched against the lumbar region of the user placing it under additional tension between attachment terminals 557 forcing it against the user's back. Thus, a portion of the load is delivered to the user directly to the lumbar area through rigid frame 511 and stretched membrane 560. The membrane 560 acts as tensile-member spring against that load and supports the user, dampens load and transfers the load into the frame, belt, and pack.

The frame member 511 for the membrane 560 can be manufactured from various materials: aluminum tube with molded elements (as depicted in the attached drawings), a plastic rigid frame, metal bars, or other rigid, or semi-rigid support structure.

The material contemplated for membrane 560 is based on the previously described synthetic crystalline material developed by ITW Dahti, Rockford, Mich., and processed by ITW-Nexus, Des Plaines, Ill. As stated, it is an elastomeric structure which forms a highly compliant membrane that offers superior comfort. The member has been designed and processed to allow for orientation of the crystalline structure to create a compliant, robust, lively and resilient spring that will not creep or sag under all operating conditions, to include high and low temperature conditions.

It must be understood that while the belt assembly is illustrated as an element of a load carrying device such as a backpack or the like, the belt 501 with active lumbar support is useful alone as a lumber support belt for users engaged in heavy lifting occupations or athletic activities.

Figure 7:
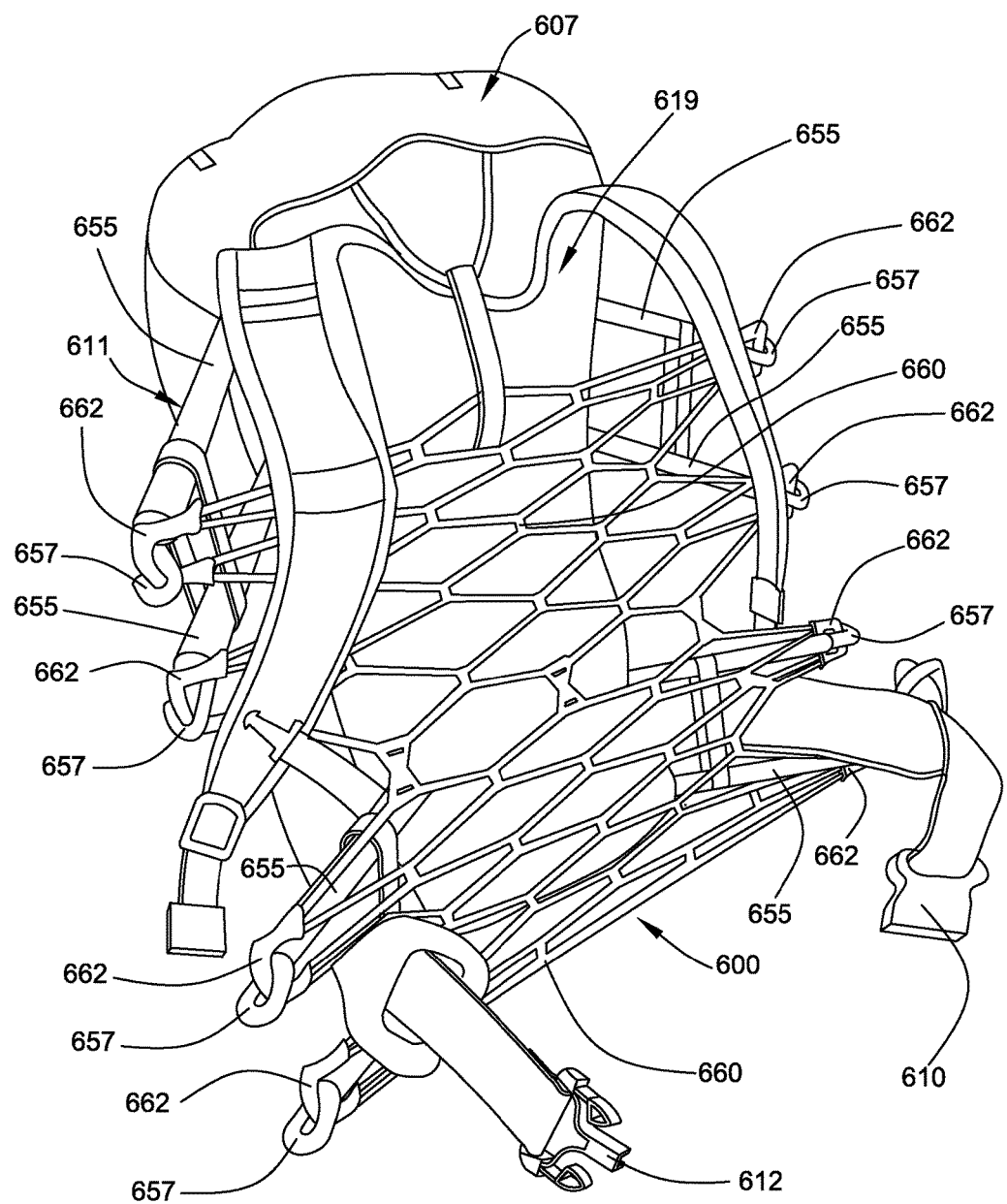
FIG. 7 is a modified form of personal equipment suspension systems with active lumbar support illustrative of the principles of the present disclosure.

FIG. 7 represent a slightly modified form of load suspension system for personal equipment load suspension utilizing the principles of this disclosure. Here a backpack assembly is provided with an expanded form of flexible suspension arrangement that includes active lumbar support. The backpack assembly includes a surrounding belt 601, and a pouch 607 supported on load suspension mechanism 619 in the form of a load receiving member connected to belt 601. Belt 601 includes buckle components 610 and 612 at opposite ends to surround the user's waist.

The flexible suspension arrangement with active lumbar support mechanism is generally designated 600 in FIG. 7.

The flexible suspension arrangement includes a rigid frame 611 with a plurality of rigid horizontal cross bars 655 spaced vertically along the load suspension mechanism 619 from the belt 601 to near the area of a user's shoulder blades. Each cross bar 655 is contoured to meet the user's shape. The horizontal cross bars 655 include attachment terminals 657 at each end.

A flexible membrane 660 is stretched between each attachment terminal 657 of horizontal cross bars 655 to form flexible support surface intended to rest upon the user's back from the waist upward toward the shoulder blade area. The membrane includes a lattice of webs 614 defining apertures 616. Ends of the webs 614 include elastomeric connection pads 662 connected to attachment terminals 657.

As load is applied to the load suspension mechanism 619, the membrane 660 acts as a tensile-member spring against that load and supports the user, dampens load and transfers the load into the frame, belt, and pack. The enlarged membrane 660 provides additional comfort through enhanced load distribution over the user's back. Membrane 660 is made of the previously described synthetic crystalline elastomeric material.

The personal equipment suspension system with active lumbar support of the present disclosure has myriad uses and applications. It may be utilized, as an example, to support a body armor vest which is normally carried upon the user's shoulders.

Body armor is an essential tool for individuals engaged in dangerous activity, such as military and law enforcement. Typically, such armor is configured as a vest with the load of the article borne by the user's shoulders.

It is a significant advantage to the user, in terms of increased comfort and decreased fatigue, if at least some of the weight of the vest is transferred to the hips and/or lumbar area. It is particularly advantageous if such transfer occurs through incorporation of a resilient membrane interposed between the load and the user's body.

With the suspension system of the present disclosure, load support is at least partially transferred to a surrounding waist belt. With the incorporation of the active lumber support, through use of lattice of resilient material between the load and the user's lumbar region the arrangement improves comfort support and ergonomics and reduces fatigue and discomfort.

The structure of the present disclosure may readily be arranged to provide the comfort and load relief advantages previously described in an armor vest application. It comprises an active lumbar support mechanism generally designated 700 interposed between the load of the body armor vest and the user's body. More particularly, the active lumbar support mechanism 700 includes a rigid frame member 711 a membrane or lattice 760 of resilient material for delivering a portion of the load to the lumbar region.

Figure 8:
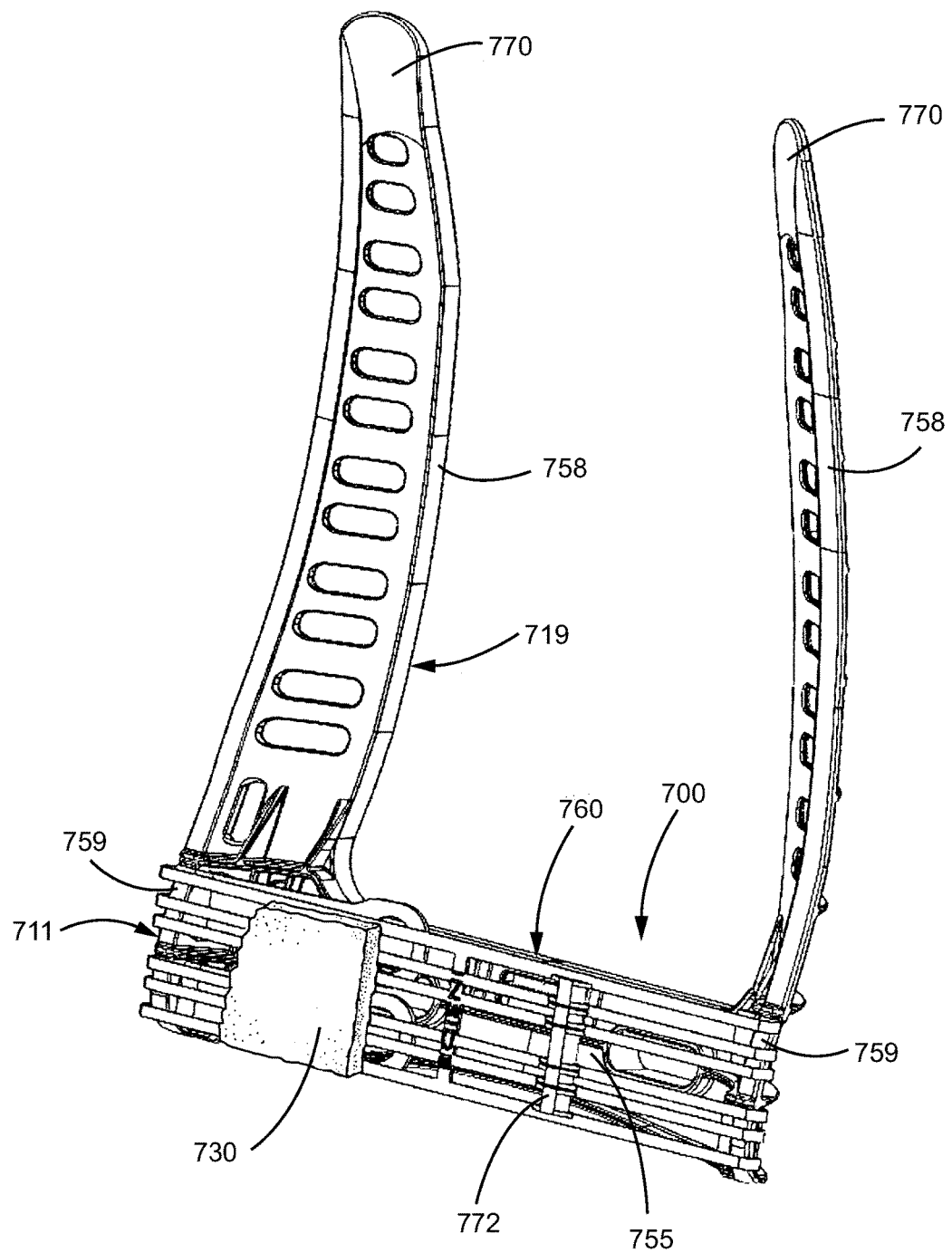
FIG. 8 is a perspective view of a personal body armor support mechanism illustrative of the principles of the present disclosure.

As seen in FIG. 8 active lumbar support mechanism 700 includes rigid frame member. Though not shown, frame member 711 would be connected to a body encircling belt with an appropriate buckle mechanism to releasably secure the frame member 711 to the user at the user's waist. A horizontal pad 730, for contact with the user's lumbar region, is supported on the rigid frame 711 by resilient lattice or membrane 760. In this embodiment, the load suspension mechanism 719 comprises a pair of spaced vertical stanchions 758 supported upon frame member 711. Load carried by the stanchions 758 is delivered to the body encircling belt through frame member 711 of the active lumbar support mechanism 700.

The active lumbar support mechanism 700 of the present disclosure may be incorporated within the fabric of the vest. An exemplary vest is a wearable article made of cloth into which is included suitable protective elements intended to provide personal safety against body piercing wounds. Typically, the protective elements, though arranged to be flexible, or soft, represent a significant load for the user because of weight. Such a vest usually includes suitable access pockets along its lower margin which can be opened for insertion of the load suspension mechanism of this embodiment, the stanchions 758.

In use, the stanchions 758 are inserted in the pocket of the vest. When a user dons the vest, the membrane pad 730 on membrane 760 rests against the user's lumbar region. At least a portion of the load of the vest is transferred through the stanchions 758, frame member 711, resilient membrane 760 and pad 730 to the user's lumbar region. In this manner, the total load of the vest is shared with the user's shoulders and also the hip, waist and lumbar area.

Alternatively, the stanchions 758 may be external to the supported vest. In such an arrangement, it is contemplated that the vest, or stanchions 758, would include attachment straps for connection to the vest.

The frame member 711 of active lumbar support mechanism 700 includes a horizontal base portion or bar 755. The opposite ends of bar 755 include a series of closely spaced vertical ribs 759 defining slots at the ends of bar 755 for connection of membrane 760. Spaced stanchions 758 extend vertically from the outer ends of bar 755. The horizontal bar 755 and stanchions 758 are curved somewhat to conform to the back of the user of the protective vest.

Stanchions 758 are of sufficient length that free ends 770 support a cloth vest at the shoulder area. The free ends 770 receive the vest load and transfer it to the bar 755 of frame member 711 and ultimately to the user's lumbar region through membrane 760 and pad 730.

The bar 755 and stanchions 758 may be integrally molded from a rigid plastic material of suitable strength. They include molded apertures or voids to reduce weight.

The resilient membrane 760 is in tension between the ends of bar 755 at ribs 759 aligned with, and spaced from, the horizontal bar 755, overlying its interior surface.

Figure 9:
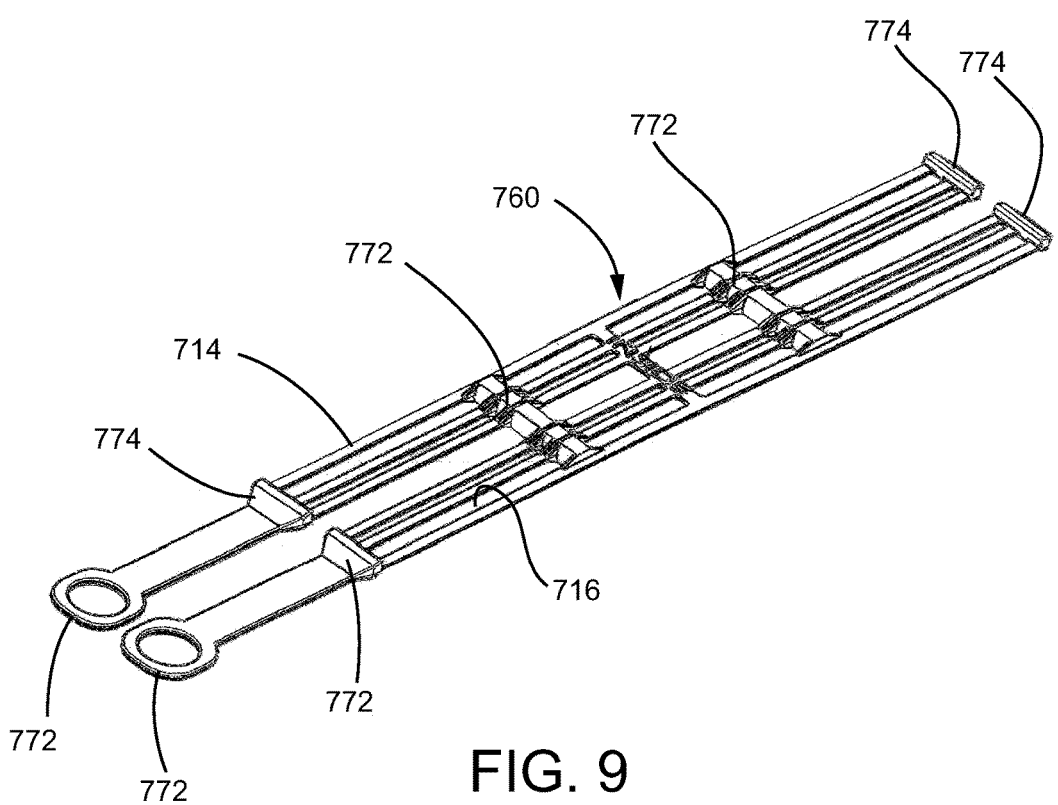
FIG. 9 is a perspective view of a portion of the apparatus of FIG. 9 illustrating the lattice membrane of the embodiment of FIG. 8.

Best seen in FIG. 9, the membrane 760 of this embodiment is a molded strap made of a lattice configuration of the previously described synthetic crystalline elastomeric material as disclosed in U.S. Pat. No. 7,441,758. It is processed to provide orientation of the crystalline structure to create a compliant, robust, lively, and resilient spring that will not creep or sag under all operating conditions.

Referring to FIG. 9 the membrane 760 is an elongate band and includes webs 714 defining apertures or voids 716. It includes two rows of nubs 772 on an interior facing surface of the membrane 760 to receive and support horizontal pad 730.

Webs 714 include spaced pairs of latching stops 774 configured to engage closely spaced ribs 759 at the opposite ends of bar 755.

The lattice configuration of the membrane and its resilient property permits attachment of the membrane 760 to ribs 759. Once attached, it presents a series of spaced elongate resilient strips in tension between the ends of bar 755.

The webs 714 of membrane 760 include pull rings 772 extending from one end for grasping the membrane 760 to resiliently stretch it for installation with latching stops 774 engaged with ribs at each end of bar 755 to retain the membrane in a pre-loaded stretched condition. When so stretched, the membrane 760 is placed in tension for resilient support of frame 711 of active lumbar support mechanism 700 upon the user at the lumbar region.

As in the earlier embodiments, the material for membrane 760 is based on the synthetic crystalline material developed by ITW Dahti, Rockford, Mich. It is an elastomeric structure which forms a highly compliant membrane that offers superior comfort. The member has been designed and processed to allow for orientation of the crystalline structure to create a compliant, robust, lively and resilient spring that will not creep or sag under all operating conditions, to include high and low temperature conditions by ITW-Nexus, Des Plaines, Ill.

As seen in FIG. 8, horizontal pad 730 is connected to membrane 760. It is thus resiliently supported upon frame 711 by membrane 760. The face of pad 730 is arranged for contact with the user's back at the lumbar area.

With the suspension system of the present disclosure, load support is at least partially transferred to a surrounding waist belt. More with the incorporation of the active lumbar support through use of a lattice of resilient material between the load and the user's lumbar region the arrangement improves comfort support and ergonomics and reduces fatigue and discomfort.

For each system embodiment disclosed, backpack belt, tool belt, lumbar belt; the elastomeric suspension membrane is supported via a rigid or semi-flexible support frame structure. The shape of the support structure can include a "pre-determined" ergonomic lumbar optimized shape form to fit the human body more precisely and comfortably. The elastomeric suspension membrane provides continuous support through complete range of motion of the user. Typical industry standard foam and gel pads provide comfort through a passive support, that compresses upon loading, and increases thermal build up in the region as well as incurring a permanent compression set. The present system is active support suspension that improves comfort, airflow and ergonomics for the user.

Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain he best modes known for practicing the invention and will enable others skilled in the art to utilize the invention. The claims are to be construed to include alternative embodiments to the extent permitted by the prior art.

The invention claimed is:

1. A personal equipment suspension system comprising:
a waist encircling belt to be worn by a user in surrounding relation to the waist, said waist encircling belt including one or more attachment devices directly secured to said waist encircling belt and,
an active lumbar support mechanism connected to said belt for positioning in association with the lumbar region of the user,
comprising a frame directly secured to the attachment device of said belt, and
a membrane of resilient synthetic crystalline elastomeric material connected to and held in tension on said frame overlying an interior surface of said belt,
wherein said membrane is sized and arranged to overlie a user's lumbar region on attachment of said belt to the user's waist, and
wherein said frame includes spaced attachment terminals and said resilient membrane comprises a lattice of resilient strips connected to said spaced attachment terminals in tension between said attachment terminals, and
wherein said frame includes at least one tubular member, said attachment terminals are positioned at opposite ends of said at least one tubular member, and
wherein said belt extends through said lattice adjacent said attachment terminals.

2. A personal equipment suspension system as claimed in claim 1 wherein said belt has an exterior surface and wherein said frame is directly connected to said exterior surface of said belt by way of the attachment device.

3. A personal suspension system as claimed in claim 1 wherein said system includes a load suspension mechanism supported by said belt, the load suspension mechanism separate from said frame.

4. A personal equipment suspension system as claimed in claim 3 wherein said load suspension mechanism comprises a backpack support.

5. A personal equipment suspension system as claimed in claim 4 wherein said frame of said active lumbar support mechanism is supported upon said load suspension mechanism and extends between a user's waist and shoulders and said membrane extends along said frame beyond a user's lumbar region.

6. A personal equipment suspension system as claimed in claim 5 wherein said frame includes spaced bars having attachment terminals and said resilient membrane comprises a lattice of resilient strips connected to said spaced attachment terminals in tension between said attachment terminals.

7. A personal equipment suspension system as claimed in claim 3 wherein said frame of said active lumbar support mechanism includes a horizontal bar and said load suspension mechanism includes spaced vertical support stanchions at opposite ends of said bar.

8. A personal equipment suspension system comprising:
a waist encircling belt to be worn by a user in surrounding relation to the waist said waist encircling belt including one or more attachment devices directly secured to said waist encircling belt,
an active lumbar support mechanism connected to said belt for positioning in association with the lumbar region of the user,
  comprising a frame directly secured to the attachment device of said belt, and
  a membrane of resilient synthetic crystalline elastomeric material connected to and held in tension on said frame overlying an interior surface of said belt and,
wherein said membrane is sized and arranged to overlie a user's lumbar region on attachment of said belt to the user's waist, and
wherein said frame includes spaced attachment terminals and said resilient membrane comprises a lattice of resilient strips connected to said spaced attachment terminals in tension between said attachment terminals, and
wherein said frame includes at least one tubular member, said attachment terminals are positioned at opposite ends of said at least one tubular member, and
wherein said system includes a load suspension mechanism supported by said belt, the load suspension mechanism separate from said frame,
wherein said frame of said active lumbar support mechanism includes a horizontal bar and said load suspension mechanism includes spaced vertical support stanchions at opposite ends of said bar,
wherein said horizontal bar includes a series of closely spaced ribs at opposite ends thereof, said resilient membrane comprises a lattice of resilient strips connected to said notches in tension at respective opposite ends of said bar.

9. A personal equipment suspension system as claimed in claim 8 wherein said bar and said stanchions are curved between said spaced support stanchions to conform to a user's back.

\* \* \* \* \*